United States Patent [19]

Hennig et al.

[11] Patent Number: 4,575,442
[45] Date of Patent: Mar. 11, 1986

[54] MAKING HEART VALVES

[75] Inventors: Ewald Hennig, Hirschhornerweg 17, D-1000 Berlin 37, Fed. Rep. of Germany; Emil S. Buecherl; Friedrich Zartnack, both of Berlin, Fed. Rep. of Germany

[73] Assignee: Ewald Hennig, Berlin, Fed. Rep. of Germany

[21] Appl. No.: 565,142

[22] Filed: Dec. 23, 1983

[30] Foreign Application Priority Data

Dec. 27, 1982 [DE] Fed. Rep. of Germany ....... 3248560

[51] Int. Cl.$^4$ .............................................. B29C 13/04
[52] U.S. Cl. .................................... 264/135; 264/269; 264/305
[58] Field of Search ....................... 264/135, 305, 269

[56] References Cited

U.S. PATENT DOCUMENTS 2,690,595 10/1954 Raiche ................................. 264/305
3,879,516 4/1975 Wolvek .............................. 264/135

Primary Examiner—James Derrington
Attorney, Agent, or Firm—Ralf H. Siegemund

[57] ABSTRACT

A heart valve is to remain with a homogenic and smooth configuration whereby particularly unevennesses tending to form loci for depositions are to be avoided. The method is basically comprised of separately forming the flap vanes through multiple coatings and the valve case is separately made but combined with the flap vane through a common coating procedure to obtain smooth transition surfaces.

4 Claims, 4 Drawing Figures

MAKING HEART VALVES

BACKGROUND OF THE INVENTION

The present invention relates to artificial heart valves being comprised of a valve case (stint) and one or several vanes or leaves arranged in the interior thereof.

Artificial heart valves have been made in the past with a variety of methods. In accordance with one approach, the valve is made through die casting or injection molding whereby the case and stint of the valve as well as the vane arranged in the interior of the case are made in one operating step. However, in accordance with the requirements for casting, the walls of any parts involved must have a certain minimum thickness. This, then, means that, on one hand, the valve case (stint) can be appropriately selected in accordance with its requirement as these requirements are such that the case wall will be thicker than the minimum thickness of the device. On the other hand, the vanes for the flaps are too thick when they have to meet the minimum thickness requirements. Accordingly, these vane and flap elements are in fact inordinately thick for satisfactory operation.

In accordance with a different method, the case for the valve is made separately from the vane and flap whereby the case, for example, is made as an annulus and the flap and vane is made separately to be connected to the case subsequently, for example, by means of bonding. This bonding by means of an adhesive is carried out manually. Moreover, it is almost inevitable that certain unevennesses appear in the transitions between vane and case. Moreover, certain adhesive residue may accumulate more or less at random. All these factors result in unevennesses of the surface of the several parts. The very fact that the material involved is inhomogenic and that the surfaces are not even, makes it inevitable that within a very short time certain deposits appear at these unevenesses which deposits are of a cellular nature and involve interalia components of the blood. As a consequence, calcification occurs subsequently and impedes the blood transmission up to a point of complete blockage.

It is an object of the present invention to provide a new and improved method for making heart valves which are homogenic from the point of view of the utilized material as well as from the point of view of surface contours whereby in particular the transition zone between the flap vanes and the case and stint does not exhibit any unevennesses that may lead to the deposit of blood residue.

In accordance with the preferred embodiment of the present invention, the following method is suggested. A core is provided as a die element having surfaces which correspond to the shape of the vanes for heart valve flaps, this core is dipped at a low speed of descent into a polymer solution having a high viscosity; after a film or coating has formed on these surfaces, the core is slowly withdrawn from the solution whereupon the core with polymer coating is dried; the foregoing i.e. the dipping and retracting is repeated several times. An independently made valve case is dipped into a polymer solution of low viscosity and held therein, the case having an interior diameter which is slightly larger than the diameter of the aforementioned core, following which the core with polymer layers is slowly inserted into the valve case and into the polymer solution contained therein, whereby upon inserting the core into the valve case, the displaced solution can continuously flow evenly from the interior of the case; subsequently the core as well as the valve case are slowly withdrawn from the solution after a period of time sufficient for the formation of a polymer coating upon the combined core and valve case configuration whereupon the core proper, following drying of the coating, is separated from the valve case and from the previously made coating, the latter having combined with the valve case coating. The viscosity of the first mentioned, i.e. high viscosity polymer solution, should be in the range from 24 to 192,000 cp and the viscosity of the low viscosity solution should be within the range from 1500 to 2000 cp. The core should have been highly polished prior to use or be provided with a coating that does not react with the polymer solution but makes sure that the surface of the thus coated core is very smooth. The polymer solution and agent is preferably a polyurethane solution.

The inventive method offers the advantage that the valve case (at least on the outside) and the flap vane are made from the same material. Moreover, the combined coating of core and valve case results in a coating that physically combines the coating for both of them so that inhomogenities and step transitions between them are avoided. In particular then there are no unevennesses formed in the surface which subsequently could establish loci for the depositing of calcium and phosphate. Moreover, the dipping method as proposed here permits the formation of very thin, film-like coatings which can be increased in thickness and width through multiple dippings. On the other hand, the valve vanes can be made of a very small wall thickness because the dipping method leads to material thickness well below the minimum thickness values that have to be observed during injection molding.

The preferred method as described above suggests the utilization of the same material for the flap vanes and the valve casing but as far as practising the method is concerned, this is not essential in principle. However, the final coating is carried out in the low polymer solution and involves the flap vanes as well as the casing in unison so that this final coating is homogenic in contour and material and it is also smooth and transitionless.

While the specification concludes with claims particularly pointing out and distinctly claiming the subject matter which is regarded as the invention, it is believed that the invention, the objects and features of the invention, and further object features and advantages thereof will better understood from the following description taken in connection the accompanying drawings in which:

Figure 1:
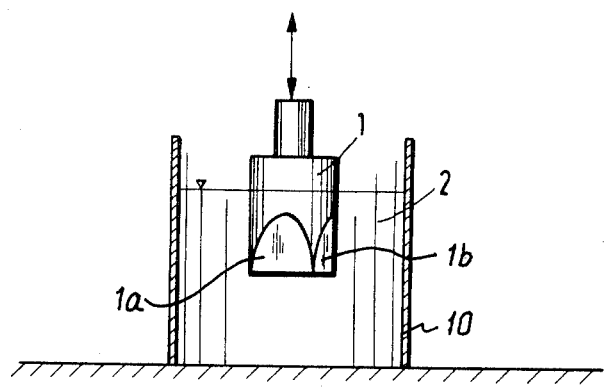
FIG. 1 illustrates the step of providing the flap vanes for a heart valve in accordance with the preferred embodiment of the present invention pursuant to practicing the best mode thereof.
Figure 2:
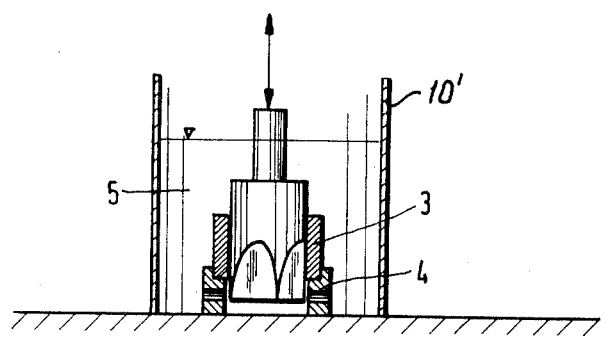
FIG. 2 illustrates the combining of the flap vanes with the casing in continuation of the process and involving particularly a second polymer solution.

Proceeding now to the detailed description of the drawings, reference is made first to FIG. 1 showing a core 1 made of high grade stainless steel, but a smoothly coated synthetic core could be used. The particular core has its front end surfaces 1a and 1b and others which are not visible in the drawing which define the contour of the flap vanes for a heart valve to be made. It is assumed in the example that the core when made of steel is polished to a very high degree. In the case of a core made of a synthetic, a particular surface coating has to be provided for initially which makes sure that the core, particularly in the shaping surfaces 1a, 1b etc. is very, very smooth.

In either case the surface portions of the core which are critical for the formation of the flap vanes are highly polished and very smooth. In the particular illustrated example, moreover, it is assumed that the vanes are of the so-called tri-leaflet configuration so that the core is in fact provided as a die element having three shaping surfaces.

The core is now dipped into a first polymer solution of polyurethane having a viscosity in the range from 24 to 192,000 cp. The core 1 is lowered into this high viscosity bath 2 in container 10 at a very slow speed which avoids the formation of bubbles or the like, which otherwise could form anywhere, the polymer material which adheres to the surface of the core should do so without the formation of any inhomogenities whatsoever. After the core and die element 1 has been dipped completely into the solution (at least as far as the relevant surfaces are concerned) the core will be retracted while a polymer film adheres to the various surface portions.

Upon completion of the withdrawal the coating will dry and subsequently dipping is repeated. The repetition of dipping can be carried out as often as necessary in order to stepwise grow the valve vanes. Since the coating in each instance is very thin, a rather fine stepwise growth is insured which means that one can, by this method, produce vanes of any desirable thickness.

In the meantime the prepared valve casing has been made separately whereby it is well possible that an appropriately shaped core has likewise dipped into a polymer solution. This prepared valve case 3 is then inserted in a low viscosity polymer solution 5 (container 10') and sits on a die element 4. The coated core 1 is then slowly inserted. The openings is die element 4 permit a discharge of solution material from the interior of the valve case 3 as the coated core is inserted. The insertion is, of course, carried out sufficiently slowly so that the outflow of low viscosity polymer solution is sufficiently slow and uniform. A uniform outflow of the material through the openings in element 4 insures that there will be no formation of bubbles or other inhomogeneities, particularly between the coated core and the valve case.

Figure 3:
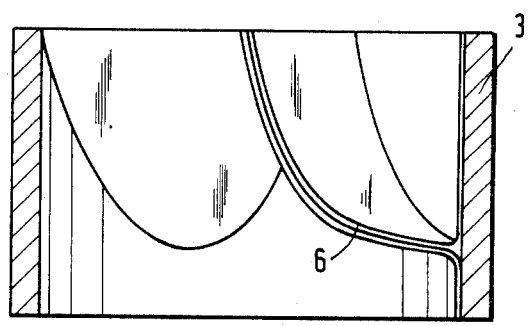
FIG. 3 is a schematic view through a portion of a valve with flap annulus with a single flap vane.
Figure 4:
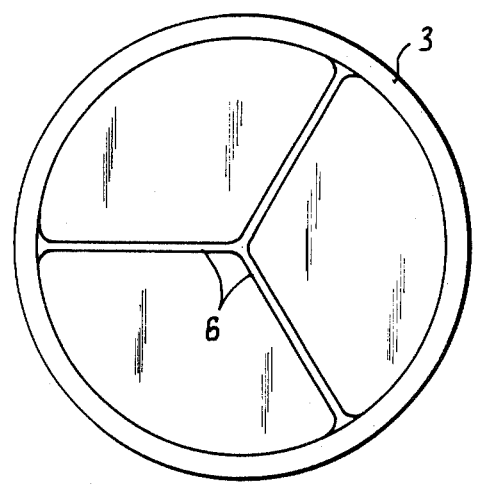
FIG. 4 is a top view of the valve shown in FIG. 3.

After insertion, core and case remain for a short period of time within the solution 5, and they are subsequently removed therefrom together; they are also dried without separating them from each other. After drying, the core 1 can easily be removed from the coated valve case whereby particularly, of course, the various and sequentially formed vane coatings (6) remain in integral configuration with the valve case coating, i.e. what is withdrawn is the core proper, the previously made coatings on the core remain adhering to and integral with the valve casing structure. Various portions may subsequently be surface finished and certain burrs along the edges may be removed. The structure then looks as shown in FIG. 3.

Finally, it should be mentioned that it is important for practicing the invention that the surfaces on the core 1 being provided for the formation of the vane leafs, including particularly the surface, and the axial extension of the core within the range of the leaf forming surfaces are somewhat larger than the axial length of the valve case.

The invention is not limited to the embodiments described above but all changes and modifications thereof not constituting departures from the spirit and scope of the invention are intended to be included.

We claim:

1. Method of making artificial heart valves, each being comprised of a case or stint and one or two leaflike flap vanes comprising the steps of providing a core having surfaces corresponding to the individual flap vanes;

slowly dipping the core into a high viscosity polymer solution;

retaining the core therein and withdrawing it slowly therefrom so that a film forms on the core surfaces;

drying the thus formed polymer film to define a coating;

repeating the three previous steps at least once to form a plurality of coatings;

providing a valve case of annular configuration having an interior diameter slightly larger than the diameter of said core;

dipping said valve case into a low viscosity polymer solution;

inserting the coated core into the valve case while in said low viscosity polymer solution whereby solution in the interior of the valve case flows out of the interior of the valve case;

retaining the core together with the valve case in said low polymer solution for a short period of time sufficient for obtaining a common coating;

slowly withdrawing the core and the valve case from the low-viscosity polymer solution;

drying the coating formed in the low viscosity polymer solution; and removing the core from its plurality of coatings and the valve case, the previously made plurality of coatings and the common coating remaining adhered to and integral with the valve case.

2. The method as in claim 1 wherein the viscosity of the high viscosity polymer solution is in the range from 24 to 192,000 cp and the viscosity of the low viscosity solution is between 1500 and 2000 cp.

3. The method as in claim 1 wherein at least the surfaces on the core to be coated with polymer that will form the flap vanes is highly polished or highly smoothed.

4. The method as in claim 1 wherein in each instance polyurethane solution is used.

* * * * *